United States Patent [19]
Lorenz et al.

[11] Patent Number: 5,948,945
[45] Date of Patent: Sep. 7, 1999

[54] PREVENTION OF SPONTANEOUS DECOMPOSITION OF GASEOUS ACETYLENE

[75] Inventors: Rudolf Erich Lorenz, Ludwigshafen; Herbert Helfert, Frankenthal; Martin Schmidt-Radde, Beindersheim; Hans-Peter Schildberg, Neustadt; Günter Saladin, Ludwigshafen, all of Germany

[73] Assignee: BASF Aktiengesellschaft, Ludwigshafen, Germany

[21] Appl. No.: 09/045,911

[22] Filed: Mar. 23, 1998

[30] Foreign Application Priority Data

Mar. 24, 1997 [DE] Germany .................. 197 12 249

[51] Int. Cl.$^6$ ................... C10L 3/00; C07C 6/00; C07C 7/10
[52] U.S. Cl. .................. 585/6; 585/534; 585/833
[58] Field of Search .................. 585/6, 534, 833

[56] References Cited

PUBLICATIONS

Kogai Shigen Kenkyusho Iho (1983), 13 (2), 23–36. Chemical Abstract (CA:100:88405)

*Primary Examiner*—Paul J. Killos
*Assistant Examiner*—J. Parsa
*Attorney, Agent, or Firm*—Oblon, Spivak, McClelland, Maier & Neustadt, P.C.

[57] ABSTRACT

A process for vinylation of an organic acidic-hydrogen compound, which entails reacting an organic acidic-hydrogen compound with acetylene or an acetylene-containing gas under elevated pressure and at elevated temperature in the presence of a base, wherein reactor regions initiating decomposition of acetylene are treated with an effective amount of a chemically inert oil of medium viscosity.

20 Claims, 1 Drawing Sheet

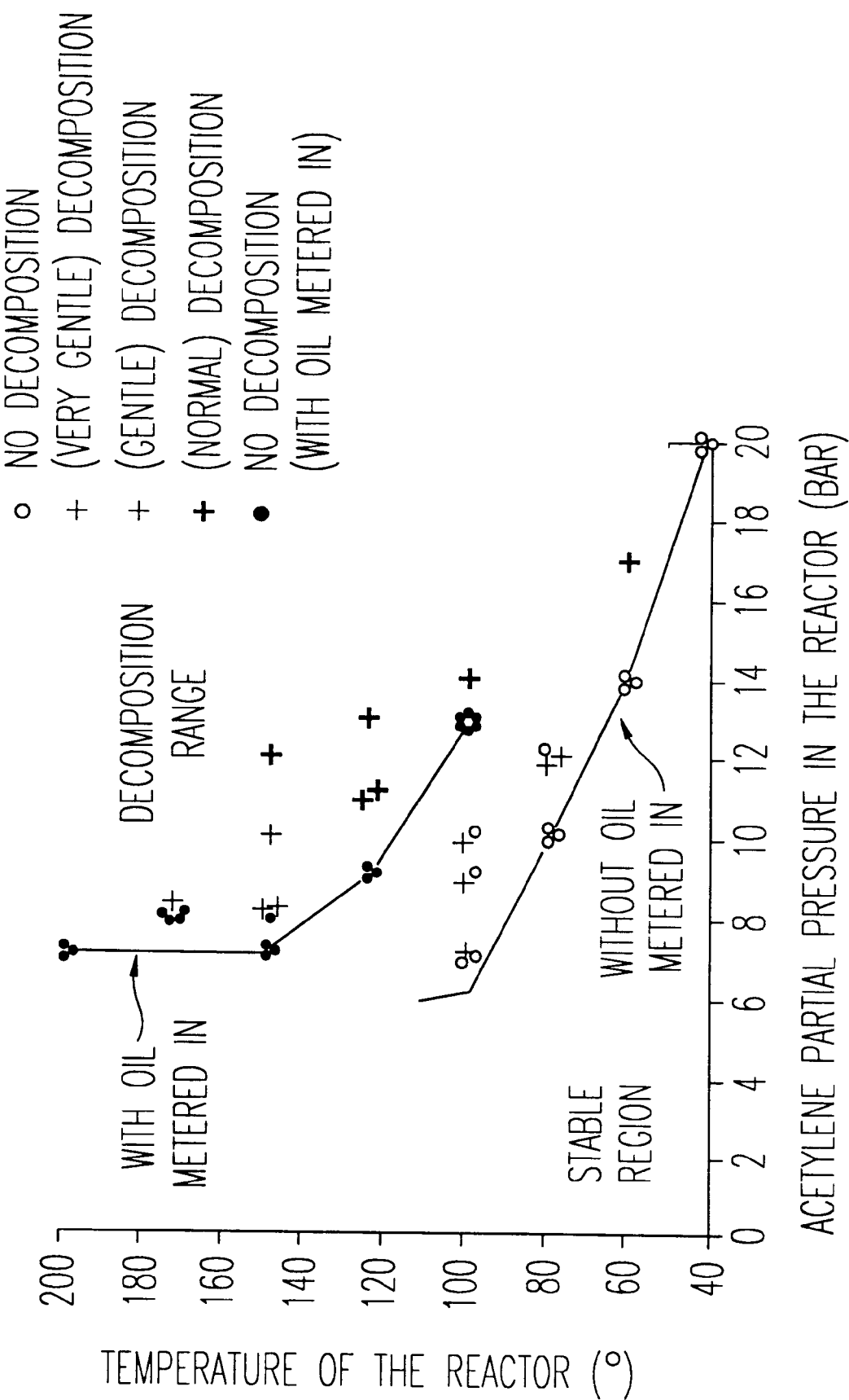

PREVENTION OF SPONTANEOUS DECOMPOSITION OF GASEOUS ACETYLENE

DESCRIPTION

The present invention relates to a method for preventing spontaneous decomposition of gaseous acetylene or gas mixtures which contain acetylene in chemical reactors. The present invention relates in particular to a method for preventing acetylene decomposition induced by chemical igniters (chemical decomposition).

It is known that acetylene and acetylene-containing gas mixtures are prone to spontaneous decomposition at elevated temperatures and under elevated pressure. The exothermic nature of these decompositions (226 kJ/mol acetylene) leads to large rises in pressure which may result in complete destruction of the reaction apparatus. It is presumed that decomposition reactions of this type are induced by chemical igniters (chemical decomposition). By chemical igniters are meant chemical compounds which, in solid form, eg. as deposits in production systems, catalyze the decomposition of gaseous acetylene. These include, besides heavy metal salts such as copper salts, in particular also bases, eg. oxo bases such as hydroxides, alcoholates, carbonates, specifically those with alkali metals as counterions, or carboxylates such as zinc stearate (see in this connection also H. P. Schildberg et al, Eighth International Symposium on Loss-Prevention and Safety Promotion in the Process Industry, Antwerp 1995). The chemical compounds mentioned as potential chemical igniters are, on the other hand, effective catalysts for chemical reactions with acetylene. It is therefore not possible to dispense with them.

It is possible in principle for chemical igniters to occur in apparatus suitable for reacting acetylene under pressure at the following points: heating coils in the autoclave, internal walls of the autoclave, acetylene inlet connectors, other connectors for introducing or removing gases. Whereas the occurrence of chemical igniters at the first two points mentioned can be prevented by relatively simple measures, such as increasing the stirrer speed, at the other points there is a danger of the reaction mixture, which is usually liquid and which contains the chemical igniters in dissolved or suspended form, being splashed there, drying on and thus producing chemical igniters in active form.

The formation of such active chemical igniters can in principle be prevented in a variety of ways. Thus, it is conceivable to rinse said points with a liquid, for example a solvent and/or a precursor, as liquid, used for the reaction. However, this results in additional costs, eg. for solvent additionally used. In the case of rinsing with precursor, this can take place only for a certain time, otherwise incomplete conversion occurs. In addition, the batch time is increased in an undesirable manner. Both variants have the disadvantage that additional amounts of liquid must be handled. Moreover both variants require an additional interface with the high pressure system of the plant which causes additional costs. As an alternative to this, rinsing said points with the liquid reaction mixture is conceivable. The handling of large amounts of liquid is disadvantageous in this variant too.

Diluting acetylene with inert gases such as nitrogen does not adequately reduce the frequency of decomposition. Moreover this measure usually increases the conversion time in an unwanted manner and reduces the conversion.

It is an object of the present invention to provide a method for preventing spontaneous decomposition of gaseous acetylene in chemical reactors which does not have the above disadvantages.

We have found that this object is achieved by preventing the spontaneous decomposition of gaseous acetylene by treating with a suitable chemically inert oil those points at which chemical igniters may occur in a reactor used for reacting acetylene.

The present invention thus relates to a method for preventing spontaneous decomposition of gaseous acetylene or gas mixtures which contain acetylene in chemical reactors, wherein at least the regions of the reactor which initiate the decomposition are treated with a chemically inert oil of medium viscosity.

The treatment according to the invention of the relevant regions of the reactor, especially the points at which deposits of chemical igniters may occur, preferably takes place in the form of an oil mist which is metered batchwise or, in particular, continuously into the reactor. In particular, the oil mist is metered in together with the gaseous acetylene.

The atomization of the oil to an oil mist takes place by conventional methods. A conventional arrangement for generating oil mists comprises, for example, a metering pump and nozzle, eg. a hollow cone nozzle, which is sited at the critical points, eg. in the region of the acetylene gas feed. To achieve effective atomization, it proves advantageous to heat the oil, for example to from 80 to 180° C., preferably from 100 to 150° C. It should be noted in this connection that effective atomization of the oil is ensured only if the oil has a suitable viscosity in the particular temperature range. Preferred oils are therefore those having a viscosity at about 100° C. of from 1 to 100 $mm^2/sec^{-1}$ preferably 2 to 80 $mm^2/sec^{-1}$ and, in particular, 5 to 50 $mm^2/sec^{-1}$ (DIN 51562 method).

The amount of oil necessary for efficient deactivation of the chemical igniters depends on the design of the reactor and is in the range from 1 to 100 ml, preferably 2 to 80 ml, in particular 5 to 50 ml, of oil per kg of acetylene and hour.

It is furthermore necessary for the oil to be chemically inert under the given reaction conditions. For this reason, the oils are preferably selected from liquid paraffins and/or synthetic oils such as polyolefin oils, eg. polyethylene oils, ester oils, water-insoluble polyglycols or silicone oils. Said oils are known to the skilled worker and are described in detail in the literature, for example in Ullmann's Enzyklopädie der technischen Chemie, 3rd edition, Volume 6, pages 718 et seq. and Volume 15, pages 278 et seq. Liquid paraffins are particularly preferred, especially those obtained by solvent refining. Oils of this type are commercially available, for example as compressor oils.

The method according to the invention for preventing spontaneous acetylene decomposition, specifically that induced by chemical igniters (chemical decomposition) has proven particularly useful in the vinylation of organic acidic-hydrogen compounds by reaction with acetylene or acetylene-containing gases under elevated pressure and at elevated temperatures in the presence of a base. Accordingly, the present invention also relates to a process for the vinylation of organic acidic-hydrogen compounds by reacting these compounds with acetylene or acetylene-containing gases under elevated pressure and at elevated temperature in the presence of a base, wherein the measures described above are used to prevent spontaneous chemical decomposition of acetylene.

Acidic-hydrogen compounds are compounds in which at least one hydrogen atom is bonded to an electronegative heteroatom, eg. oxygen or nitrogen. Examples of suitable acidic-hydrogen compounds comprise linear or branched alkanols with 1 to 30 carbon atoms, such as methanol, ethanol, n-propanol, i-propanol, n-butanol, isobutanol, tert-butanol, n-pentanol, neopentyl alcohol, tert-amyl alcohol, 1-hexanol, 2-ethyl-1-hexanol, 2-propyl-1-heptanol, n-octanol, n-decanol, n-dodecanol, n-tetradecanol, stearyl alcohol, hydroxymethylcyclohexane, cycloalkanols such as cyclopentanol or cyclohexanol, diols such as ethylene glycol, diethylene glycol, triethylene glycol, tetraethylene glycol or higher polyethylene glycols with molecular weights in the range from 200 to 500, 1,4-bis (hydroxymethyl)cyclohexane, 1,6-hexanediol, 1,2- or 1,3-propanediol, 1,2-, 1,3- or 1,4-butanediol, poly(1,4-butanediol) with molecular weights in the range from 150 to 500, the mono-$C_1$–$C_4$-alkyl ethers of said diols, amino alcohols such as 3-amino-1-propanol, 4-amino-1-butanol and their mono- or di-$C_1$–$C_4$-alkyl derivatives, eg. mono- or dimethylamino-1-propanol, mono- or diethylamino-1-propanol, or polyols such as glycerol, trimethylolpropane or pentaerythritol. The acidic-hydrogen compounds furthermore include compounds containing NH or $NH_2$ groups, preferably those in which the acidity of the NH hydrogen is increased, for example linear, branched or cyclic amides (lactams), eg. the amides of aliphatic $C_1$–$C_4$-carboxylic acids, such as formamide, acetamide etc., pyrrolidone or caprolactam, urea and its derivatives such as N-alkyl- or N,N'-dialkylureas, imidazolidones or nitrogen heteroaromatic compounds such as imidazole, pyrazole, carbazole and substituted and/or partially hydrogenated derivatives thereof such as 2-methylimidazoline. Also included here are carbon acid compounds such as dialkyl malonates and their derivatives, eg. dimethyl or diethyl malonate, diethyl α-methylbutylmalonate, cyanoacetic esters, eg. methyl or ethyl cyanoacetate, and malononitrile. Compounds containing OH groups are preferred.

Said compounds are preferably reacted in the presence of oxo bases. By these are meant hydroxides, alcoholates such as methanolate, ethanolate, n- or isopropanolate, n-, 2- or tert-butanolate, carbonates or carboxylates such as acetate or stearate. Particularly used as oxo bases are alkali metal hydroxides or alkali metal alcoholates such as potassium hydroxide or potassium methanolate. The reaction can be carried out without diluent or in a preferably polar aprotic solvent such as a cyclic ether, eg. tetrahydrofuran, or an amide, eg. dimethylformamide, dimethylacetamide, N-methylpyrrolidone.

The reactions require the use of acetylene partial pressures in the range from 2 to 50 bar, preferably 10 to 30 bar, and temperatures in the range from 50 to 200° C., preferably 100 to 45 180° C. Under these conditions, said oxo bases, especially potassium hydroxide, prove to be particularly active chemical igniters (see H. Schildberg et al). The oil used for deactivation is preferably introduced through the acetylene feed. An optimal amount of oil is about 1–5 l/h for a total batch size of 1 ton.

Examples of products obtainable in this way comprise the monovinyl ethers of the abovementioned alcohols, eg. ethyl vinyl ether, n-propyl vinyl ether, isopropyl vinyl ether, n-butyl vinyl ether, isobutyl vinyl ether, tert-butyl vinyl ether, tert-amyl vinyl ether, ethylhexyl vinyl ether, dodecyl vinyl ether, octadecyl vinyl ether, ethylene glycol methyl vinyl ether, ethylene glycol butyl vinyl ether, cyclohexyl vinyl ether, di-, tri- or tetraethylene glycol methyl vinyl ether, the mono- and divinyl ethers of the abovementioned diols such as ethylene glycol monovinyl ether and divinyl ether, 1,4-butanediol monovinyl ether and divinyl ether, 1,6-hexanediol monovinyl ether and divinyl ether, 1,4-bis (hydroxymethyl)cyclohexane monovinyl ether and divinyl ether, di-, tri- and tetraethylene glycol monovinyl ether and divinyl ether, poly(1,4-butylene glycol) monovinyl ether and divinyl ether, also 3-amino-1-propanol vinyl ether or 3-diethylaminopropanol vinyl ether, 1-vinylimidazole (from imidazole), 1-vinylimidazoline (from imidazoline), 1-vinyl-2-methylimidazoline (from 2-methylimidazoline), N,N'-divinylethyleneurea (from urea), N-vinylformamide (from formamide), N-vinylacetamide (from acetamide), N-methyl-N-vinylacetamide (from N-methylacetamide), N-vinylpyrrolidone (from pyrrolidone), N-vinyl-2-piperidone (from 2-piperidone) and N-vinylcaprolactam (from ε-caprolactam).

Effective suppression of spontaneous acetylene decomposition in reactions of these types is ensured merely by generating the oil mist according to the invention in the acetylene feed line, preferably in the region where the acetylene feed line enters the reaction vessel.

The method according to the invention thus results, especially in these reactions, in effective prevention of spontaneous acetylene decomposition.

EXAMPLE

Determination of the tendency of gaseous acetylene to decompose in the presence of KOH as chemical igniter The invention is now explained in detail with reference to FIG. 1. The oil used was the compressor oil Wiol® CT 220 supplied by Wintershall (mineral oil; DIN 51757 density at 15° C.: 0.894 g/cm$^3$; DIN 51562 viscosity at 100° C.: 17.6 mm$^2$/s; DIN ISO 2909 viscosity index: 85; DIN 51423 refractive index: $n_D^{20}$=1.490; DIN 51775 aniline point: 117° C.). The metering device consisted of an oil container with a metering piston pump and a hollow cone nozzle with a bore diameter of 0.1 mm. The nozzle was sited immediately upstream of the high-pressure valve on the acetylene connector. The investigation of acetylene decomposition was carried out in a soot-free 2.5 l autoclave. For this purpose, 4 g of potassium hydroxide in a porcelain dish were placed in the autoclave and, after flushing with nitrogen, an acetylene/nitrogen mixture was fed into the autoclave until the total pressure was 20 bar. The autoclave was then heated above 200° C. It was noted whether decomposition took place and, if so, how violently. The tests were carried out both without and with oil injection (about 5 ml/h). The oil was heated to 120° C. before spraying in.

The results are summarized in FIG. 1: FIG. 1 shows a pressure-temperature diagram of the frequency and violence of acetylene decomposition in nitrogen/acetylene gas mixtures in the presence of KOH under 20 bar. In this, circles represent pressure/temperature values at which no decomposition was observed even without oil injection. Crosses represent pressure/temperature values at which spontaneous acetylene decomposition took place. On use according to the invention of an oil mist there was no longer decomposition at pressure/temperature ratios at which decomposition took place without the measure according to the invention (bullets).

We claim:

1. A process for vinylation of an organic acidic-hydrogen compound, which comprises reacting an organic acidic-hydrogen compound with acetylene or an acetylene-containing gas under elevated pressure and at elevated temperature in the presence of a base, wherein reactor regions initiating decomposition of acetylene are treated with an effective amount of a chemically inert oil of medium viscosity.

2. The process of claim 1, wherein the organic acidic-hydrogen compound is selected from the group consisting of alkanols, glycols and polyols.

3. The process of claim 2, wherein said organic acidic-hydrogen compound is selected from the group consisting of linear and branched alkanols having from 1 to 30 carbon atoms.

4. The process of claim 3, wherein said organic acidic-hydrogen compound is a glycol having a molecular weight in the range of from about 200–500.

5. The process of claim 1, wherein said organic acidic-hydrogen compound contains —NH— or —NH$_2$ groups.

6. The process of claim 5, wherein said organic acidic-hydrogen compound is selected from the group consisting of amides of $C_1$–$C_4$-carboxylic acids, pyrrolidone, caprolactam, urea, N-alkyl ureas, N,N'-dialkylureas, imidazolidones, imidazole, pyrazole, carbazole and 2-methylimidazoline.

7. The process of claim 1, wherein said organic acidic-hydrogen compound is a carbon acid compound selected from the group consisting of dialkylmalonates, cyanoacetic esters and malononitrile.

8. The process of claim 7, wherein said organic acidic-hydrogen compound is a dialkyl malonate selected from the group consisting of dimethyl, malonate diethyl malonate and diethyl α-methylbutyl malonate.

9. The process of claim 7, wherein said organic acidic-hydrogen compound is a cyanoacetic ester selected from the group consisting of methyl cyanoacetate and ethyl cyanoacetate.

10. The process of claim 1, which is conducted under a pressure of from about 2 to 50 bar and at a temperature in the range of from about 50 to 200° C.

11. The process of claim 10, which is conducted under a pressure of from about 10 to 30 bar and at a temperature of from about 100 to 180° C.

12. The process of claim 1, wherein said medium viscosity oil has a viscosity of about 100° C. of from about 1 to 100 mm$^2$/sec$^{-1}$.

13. The process of claim 12, wherein said medium viscosity oil has a viscosity at about 100° C. of from about 2 to 80 mm$^2$/sec$^{-1}$.

14. The process of claim 12, wherein said medium viscosity oil has a viscosity at about 100° C. of from about 5 to 50 mm$^2$/sec$^{-1}$.

15. The process of claim 1, wherein said medium viscosity oil is selected from the group consisting of liquid paraffins.

16. The process of claim 15, wherein said liquid paraffins are obtained by solvent refining.

17. The process of claim 1, wherein said medium viscosity oil is a synthetic oil selected from the group consisting of polyolefin oils, ester oils, water-insoluble polyglycols and silicone oils.

18. The process of claim 1, wherein said effective amount of said medium viscosity oil is from about 1 to 100 ml of oil per kg of acetylene per hour.

19. The process of claim 18, wherein said amount is from about 2 to 80 ml of oil per kg of acetylene per hour.

20. The process of claim 19, wherein said amount is from about 5 to 50 ml of oil per kg of acetylene per hour.

* * * * *